United States Patent [19]

Smith

[11] Patent Number: 5,512,471
[45] Date of Patent: Apr. 30, 1996

[54] PROCESS FOR PURIFYING AN α-D-GALACTOSIDASE ISOZYME FROM COFFEA BEANS

[75] Inventor: Daniel S. Smith, Columbia, Mo.

[73] Assignee: The Curators of the University of Missouri, Columbia, Mich.

[21] Appl. No.: 996,029

[22] Filed: Dec. 23, 1992

[51] Int. Cl.$^6$ .................................................. C12N 9/40
[52] U.S. Cl. ........................... 435/208; 435/814; 435/815
[58] Field of Search .................................. 435/208, 814, 435/815

[56] References Cited

PUBLICATIONS

Courtois et al (1966) Methods in Enzymology VIII, pp. 565–571.
Chinen et al (1981) Journal of Biochemistry 90, pp. 1453–1461.
Dey 10(1984) Eur. J. Biochemistry 140, pp. 385–390.
Yagi et al. (1990) Archives of Biochemistry and Biophysics 280, pp. 61–67.
Harpal et al (1974) Biochimica et Biophysica Acta 341, pp. 213–221.
Hemingway et al Chemistry and Significance of Condensed Tannins, Plenum Press: 1988, pp. 323–334.
H. Flowers et al., *Adv. Enzymol.* 48:29–95 (1979).
M. Corchete et al., *Phytochemistry* 26:927–932 (1987).
S. Yatziv et al., *Biophys. Res. Comm.* 45:514–518 (1971).
J. Courtois et al., *Methods Enzymol.* 8:565–570 (1966).
L. Lenny et al., *Blood* 77:1383–1388 (1991).
N. Harpaz et al., *Arch. Biochem. and Biophys.* 170:676–683 (1975).
J. Goldstein et al., *Phytochemistry* 4:185–192 (1965).
N. Harpaz et al., *Methods Enzymol.* 34:347–350 (1974).
M. Bradford, *Anal. Biochem.* 72:248–254 (1976).
K. Dean et al., in *Practical Enzymology of the Sphingolipidoses* (R. Glew and S. Peters, Eds, A. R. Liss, Inc., N.Y.) pp. 202–204.
U. Laemmli, *Nature* 227:680–685 (1970).
S. Moore et al., *Biol. Chem.* 211:907–913 (1954).
S. Twining, *Anal. Biochem.* 143:30–34 (1984).
N. Bryant, In *Immunohematology* (W.B. Saunders Co., Philadelphia) pp. 280–297 (1976).
A. Hagerman, In *Chemistry and Sig. of Cond. Tannins* (Plenum Press, N.Y.) pp. 323–334 (1989).
K. Gutowski et al., *Carbohydr. Res.* 178:307–313 (1988).
Sigma Catalogue, 1983, p. 659.
Hailbach et al (Dec. 1991) Biochemical and Biophysical Research Communications 181, pp. 1564–1571.
Nyman (1985) Phytochemistry 24, pp. 2939–2944.
Carchon et al (1975) Carbohydrate Research 41, pp. 175–189.
Dey et al (1983) The Journal of Biological Chemistry, 258, pp. 923–929.

*Primary Examiner*—David M. Naff
*Assistant Examiner*—Michael V. Meller
*Attorney, Agent, or Firm*—Kohn & Associates

[57] ABSTRACT

A *Coffea canephora*-D-galactosidase isozyme is purified by extracting a supernatant from Coffea beans containing the isozyme, extracting tannin from the supernatant, and isolating the isozyme. Preferably, the supernatant is extracted by exposing the supernatant to insoluble polyvinylpolypyrrolidone in an amount sufficient to remove the tannin from the supernatant by forming hydrogen bonds with the tannin.

19 Claims, 2 Drawing Sheets

PROCESS FOR PURIFYING AN α-D-GALACTOSIDASE ISOZYME FROM COFFEA BEANS

TECHNICAL FIELD

The present invention relates to a process for purifying an isozyme whose source contains tannin resin. The purified enzyme per se is also disclosed. Such enzymes are useful in the enzymatic conversion of blood type B to blood type O.

BACKGROUND OF THE INVENTION

Exoglycosidases are enzymes which can modify cell membrane carbohydrate epitopes and thereby modify the immune response. More particularly, such enzymes can be used in the process of converting types A, B, and AB, red blood cells to universally transfusible type O cells. The U.S. Pat. No. 4,330,619, issued May 18, 1982; U.S. Pat. No. 4,427,777, issued Jan. 24, 1984, and 4,609,627, issued Sep. 2, 1986, all to Goldstein, all disclose methods and enzymes useful in the enzymatic conversion of red blood cells for transfusion purposes.

α-D-galactosidases [EC 3.2.1.22] are a common class of exoglycosidases. Although physical properties of these enzymes differ as a group, and the physiological significance of these enzymes are not clearly established, isozymes of α-D-galactosidase are common to many plant species (1,2). Several investigators have studied α-D-galactosidase from Coffea (3). There are reports that several isozymes exist for the Coffea α-D-galactosidase enzyme (4).

Although research has been conducted with regard to the use of Coffea α-D-galactosidase for cell membrane modification studies, there has not been to date a publication throughly characterizing substrate specificity, physical characteristics, detectable protease activity, or detailed data proving homogeneity in the preparation used in those studies (5).

The *Coffea canephora* enzyme has special significance because of its specificity and pH optimum. The enzyme degrades the blood type B antigen creating the less immunogenic blood type O (6). Such activity can have great significance with regard to its use in the enzymatic conversion of erythrocytes from blood type B to O, thereby enlarging the compatible blood supply.

Tannins inhibit enzymes, precipitate proteins, and in the presence of oxygen, tannins generate quinones that covalently bind proteins (7). Since tannin is abundant in Coffea beans, the rapid and efficient removal of tannin resins has been determined to be desirable.

Tannin extractions from various preparations have been reported. Original methods for tannin extraction from coffee beans were described by several investigators (4,8). The tannin was removed from bean meal by sequential extractions with benzene or acetone/toluene. Acetone, toluene, and benzene are flammable; benzene is carcinogenic; and all are difficult to dispose of safely. Furthermore, several long extractions were required and it was difficult to remove all of the tannin. Preliminary experiments by Goldstein et al have shown that treatment of enzyme/tannin mixtures with certain high molecular weight polymers preserves enzymatic activity while removing tannin (7).

The present invention provides a process by which extraction of tannin from a supernatant derived from a Coffea bean homogenate results in a purified α-D-galactosidase isozyme having significantly increased activity.

SUMMARY OF THE INVENTION

In accordance with the present invention, a process for purifying a *Coffea canephora* α-D-galactosidase isozyme includes the steps of extracting a supernatant from Coffea beans containing the isozyme, extracting tannin from the supernatant, and isolating the purified isozyme. The invention further provides a purified α-D-galactosidase isozyme characterized by a. having a molecular weight of 36.7 kDa by SDS PAGE and 34.0 kDa by gel filtration and being highly selective for α-D-galactosides. The enzyme has a protease activity below detectable limits and a broad pH optimun at 6.3, and an approximate pI of 7.03. The enzyme is unaffected by ionic strength, is stable at 4° C., and hydrolyzes the terminal α-D-galactosyl residue from the blood type B epitope.

FIGURES IN THE DRAWINGS

Other advantages of the present invention will be readily appreciated as the same becomes better understood by reference to the following detailed description when considered in connection with the accompanying drawings wherein:

FIG. 1a shows the results of SDS PAGE separation. In lane 1 are molecular weight standards 97.4, 66.2, 45.0, 31.0, 21.5, and 14.4 kDa, and in lanes 2 and 3 are reduced (M.W. = 36.7 kDa) and unreduced (M.W. = 32.1 kDa) galactosidase, respectively;

DETAILED DESCRIPTION OF THE INVENTION

Figure 1A:
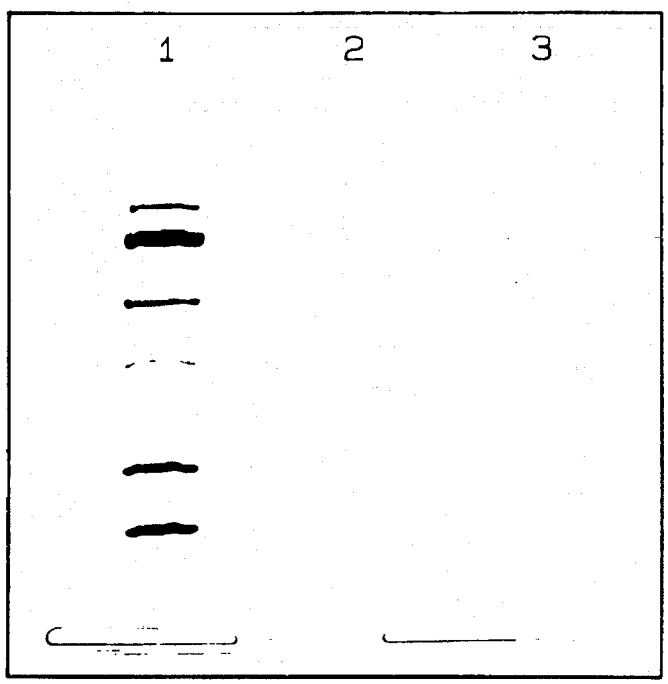
FIG. 1b is a graph showing the gel filtration molecular weight standards (□) and the α-D-galactosidase (O,M.W.= 34.0 kDa)

The present invention provides a process for purifying *Coffea canephora* α-D-galactosidase enzyme by the general steps of extracting a supernatant from Coffea beans containing the isozyme, extracting tannin from the supernatant, and isolating the purified isozyme.

More specifically, the supernatant is extracted from the Coffea beans by homogenizing the Coffea beans, such as in a Waring blender. Prior to homogenization, the beans can be soaked in deionized water, causing the passive release of tannin into the water. It was determined that after three days of soaking, release of tannin into the water had decreased.

More complete extraction of the tannin from the supernatant is accomplished by the addition of polyvinylpolypyrrolidone (PVPP) (Sigma Corp., Cat. No. P6755, Polyclar AM™ from GAF Corp. to the extraction buffer. PVPP is an insoluble, high molecular weight, cross-linked form of polyvinylpyrrolidone.

Various buffers can be used for the extraction. The extraction buffer must efficiently solubilize the enzyme. Generally, buffers with a pH in the range of 3.0 to 9.0 are desirable. The ionic strength of the buffer is not critical but is usually above 0.001. Buffer species with pKa values in the range of 3.0 to 9.0 are desirable. Preferably, sodium citrate is used as the extraction buffer. The sodium citrate can be used in a range of 0.1 to 500.0 mM at pH range of 2.0 to 10.0. Preferably, 25 mM sodium citrate is used at pH 5.0. The buffer can contain 0.01 to 20.0 percent (w/v) PVPP. Preferably, the buffer contains 10 percent PVPP. Since the PVPP is insoluble in the buffer, after incubation of the extraction buffer with the homogenate for a period of time, preferably thirty minutes, the PVPP which has extracted tannin from the homogenate can be pelleted by centrifugation. Repetition of this step insures quantitative extraction of the PVPP and bound tannin from the preparation.

Once the supernatant is decanted from the PVPP pellet, and Tween 80 is added to 0.1 percent (w/v) concentration. The enzyme is precipitated by addition of ammonium sulfate. The precipitate can be harvested by centrifugation. Once resuspended into a buffer containing Tween 80, the suspended enzyme is dialyzed exhaustively into the same buffer. Tween 80 dissociates residual tannin from the enzyme. Tween 80 is a nonionic detergent and is a monooleate of polyoxyethylenesorbitan with a fatty acid composition of approximately 75 percent oleic acid and the balance linoleic, palmitic and stearic acids.

Examples of buffers usable in this resuspension and dialysis step are TRIS-HCl, sodium phosphate, sodium citrate, or any buffer with a pKa in the range of 5.0 to 8.0.

Preferably, sodium citrate buffer is utilized for the resuspension. The buffer can be in the range 0.1 to 500.0 mM and 3.0 to 9.0 pH. Preferably, the sodium citrate is a 20.0 mM buffer at pH 7.0. The buffer can contain 0.0001 to 1 percent (w/v) Tween 80 and preferably 0.1 percent Tween 80.

The dialyzed preparation is then applied to a DEAE-Sephadex column equilibrated in the sodium citrate buffer containing Tween 80. The column flow through is then collected and dialyzed into another sodium citrate buffer containing Tween 80 at a lower pH. The preferred conditions for the column and dialysis buffer are as follows:

pH range 2 to 9 preferably 4.5.

Citrate buffer with concentration range of 0.5 to 400 mM preferably 5 mM.

Tween concentration range of 0.0001 to 1.0 percent preferably 0.1 percent.

The dialyzed preparation is then loaded onto a SP-Sephadex column equilibrated in the sodium citrate buffer containing the Tween 80. As set forth below, further dialysis steps can be conducted prior to applying the pooled active fractions to an α-D-galactosidase Affi-Gel 10 column. As described below in the Experimental section, active fractions of highly purified enzymes can be pooled from these columns and again dialyzed in the sodium citrate buffer containing the Tween 80.

It is critical that each of the tannin extraction steps be carried out to provide the increased enzyme activity as reported below in the Experimental section. Such high activity renders the resultant Coffea α-D-galactosidase an excellent tool for large scale enzymatic conversions of human blood type B red blood cells to universally transfusable O cells.

The following Experimental section provides a specific extraction process and analytical procedure characterizing the derived purified enzyme. The purified enzyme has an activity significantly greater than those reported in the above cited Goldstein patents, the prior art not recognizing the criticality of the removal of the tannin resin nor the ability to maintain a high activity of the enzyme after the extraction steps are completed.

EXPERIMENTAL EVIDENCE

MATERIALS AND METHODS

Chemicals: Affi-Gel 10 and SDS polyacrylamide gels were purchased from Bio-Rad, Richmond, Calif. Endoprotease substrates were obtained from Boehringer Mannheim, Indianapolis, Ind. All other chemicals, substrates, and chromatography resins were of the highest purity available from Sigma Chemical Company, St. Louis, Mo., or Aldrich, Milwaukee, Wis. Antisera was purchased from Immucor, Norcross, Ga. and Ortho Diagnostic Systems, Raritan, N.J. Green *Coffea canephora* beans were obtained from a local commercial supplier. Human erythrocytes were obtained from a local blood center and rabbit erythrocytes were obtained from anesthetized animals. The affinity ligand, ε-amino-hexanoly-α-D-galactopyranosylamine, was synthesized by a modification of the method of Harpaz et al (8). Purity of the product was determined by thin-layer chromatography and mass spectroscopy. The ligand was coupled to Affi-Gel 10 per the manufacturers directions. Coupling efficiencies of 80% with calculated affinity resin ligand concentrations of approximately 4 mM were achieved.

Purification of the enzyme:

Step 1. Each of the following steps was carried out at 4° C. in subdued light to minimize proteolysis and quinone production. 200 g of dry beans were allowed to soak for three days in deionized water which was changed daily. At the end of three days, tannin release into the water had abated. The beans were drained, washed, and homogenized in a Waring blender with one liter of 25 mM Na citrate +10 percent (w/v) polyvinylpolypyrrolidone (PVPP), pH =5.0. The resulting slurry was allowed to incubate with occasional stirring for 30 minutes and centrifuged at 6,844×g for 30 minutes. The supernatant was decanted and mixed with another liter of the above solution for 30 minutes. The PVPP was once again pelleted by centrifugation. To the supernatant, Tween 80 was added to a 0.1 percent (w/v) concentration and ammonium sulfate was slowly added to 65 percent (w/v) and allowed to incubate for one hour. The precipitate was harvested by centrifugation at 6,844 ×g for one hour. The precipitate was reserved, suspended in a minimum volume of water, and dialyzed exhaustively into 20 mM Na citrate +0.1 percent Tween 80, pH=7.0.

Step 2. The dialysate was loaded onto a 2.5 ×20 cm DEAE-Sephadex A-50 column equilibrated in 20 mM Na citrate +0.1 percent Tween 80, pH =7.0. The flow through was collected and dialyzed exhaustively into 5 mM Na citrate +0.1 percent Tween 80, pH = 4.5.

Step 3. The dialyzed preparation was loaded onto a 2.5 ×10 cm SP-Sephadex C-50 column equilibrated in 5mM Na citrate +0.1 percent Tween 80, pH = 4.5. The column was then washed with 90 mls of 55 mM Na citrate +0.1 percent Tween 80, pH =4.5. The enzyme was eluted with 50 mM Na citrate +500 mM NaCl+0.1 percent Tween 80, pH = 7.0. Active fractions were pooled and dialyzed into 25 mM Na citrate + 0.1 percent Tween 80, pH = 4.5.

Step 4. After dialysis the pool was applied to a 1.5 ×20 cm ε-Affi-Gel 10 column equilibrated in 25 mM Na citrate + 0.1 percent Tween 80, pH = 4.5. The column was then washed with 90 mls of 25 mM Na citrate + 0.1 percent Tween 80, pH = 4.5. The enzyme was eluted with 50 mM Na citrate + 100 mM methyl-α-D-galactopyranoside + 0.1 percent Tween 80, pH =7.5. Active fractions were pooled and dialyzed into 25 mM Na citrate + 0.1 percent Tween 80, pH = 6.0.

Analytical procedures: Protein concentration was quantitated by the method of Bradford using bovine serum albumin (BSA) as a standard (9). Enzymatic activity was quantitated by measuring the production of p-nitrophenol (PNP) upon incubation of enzyme aliquots in 200 µl of 50 mM Na citrate +1 mg/ml BSA + 2.5 mM PNP-α-D-galactopyranoside, pH = 5.0, at 37° C. The reactions were quenched with 1.0 ml of 250 mM $Na_2CO_3$ and the OD 405 nm was measured. One unit of activity was defined as 1.0 µmole of substrate hydrolyzed per minute. Substrate specificity studies were performed in the same buffer but with PNP conjugates at a 2.5 mM concentration and pH = 6.0. Activity against the 4-methylumbelliferyl (4-MU) substrates was performed by an adaption of the method of Dean et al at pH = 6.0 (10).

The pH optimum was determined by incubating aliquots of the enzyme in 40 mM Na citrate +40 mN Na $H_2PO_4$+1 mg/ml BSA+2.5 mM PNP-α-D-galactopyranoside, pH = 2.0 to 8.0. The ionic strength optimum was determined by incubating aliquots of the enzyme in 5.0 mM Na citrate +1 mg/ml BSA +2.5 mM PNP α-D-galactopyranoside +0 to 1.0M Na Cl, pH = 6.0. The Km for PNP-α-D-galactopyranoside was determined by varying the substrate concentration in 50 mM Na citrate +1 mg/ml BSA, pH =6.0. The native molecular weight of the isozyme was determined by applying a concentrated portion of the enzyme to a 1.5×45 cm Sephacryl S-200 column equilibrated in 25 mM Na citrate +200 mM NaCl, pH=6.0.

SDS polyacrylamide gel 16 PAGE) was performed according to the method of Laemmli and the protein bands developed with Coomassie Blue R-250, a staining dye (11). The pI was approximated by chromatofocusing a concentrated portion of enzyme on a 1.0×18 cm PBE 94 column equilibrated in 25 mM ethanolamine, pH =9.4. The column was developed with a 1:10 dilution of Polybuffer 96, pH = 6.0. Polybuffer 96™ is an ampholyte solution for chromatofocusing commercially available from Pharmacia Fine Chemicals, Uppsala, Sweden. Enzymatic activity and pH were quantitated in the effluent. Amino acid composition was determined on a Beckman amino acid analyzer by standard methods (12).

Aminopeptidase assays were performed by incubating aliquots of enzyme with 2.5 mM of various paranitranilide (PNA) substrates in 200 µl of 50 mM Na citrate +50 mM $NaH_2PO_4$+0.1 percent Tween 80, pH =5.0 to 8.0. The reactions were incubated at 37° C., quenched with 1.0 ml of 250 mM $Na_2CO_3$, and the OD 405 nm was determined. One unit of aminopeptidase activity was defined as 1.0 µmole of PNA hydrolyzed per minute. Endoprotease assays were performed by an adaptation of the resorufin-labeled casein assay of Twining (13). The limit of sensitivity was determined using a trypsin standard.

Activity against the erythrocyte human blood group B and rabbit pentasaccharide ceramide antigen was determined by incubating 15 units of detergent free isozyme with 150 µl of erythrocytes in 25 mM Na citrate +25 mM $NaH_2PO_4$+ 100 mM NaCl, pH =5.8, at 37° C. for three hours. The cells were washed with 25 mM $NaH_2PO_4$+150 mM NaCl, pH =7.0, and then incubated with varying dilutions of polyclonal anti-B serum or monoclonal antibody active against pentasaccharide ceramide. Hemagglutination was performed and titer scored by standard methods (14).

With a higher concentration of enzyme and/or a higher hematocrit, seroconversion of erythrocytes can be achieved at 24° C. Detergent-free concentrated enzyme for enzymatic conversion is prepared by ion exchange chromatogrpahy on SP Sephadex.

RESULTS AND DISCUSSION

As shown in Table 1, rapid purification of the α-D-galactosidase isoenzyme was achieved with acceptable recoveries of active protein. Tannin bound quickly and with high specificity to the PVPP included in the homogenization buffer (15). Tween-80 was also used in the purification to enhance tannin protein dissociation. Unexpectedly, the steps did not negatively affect enzymatic activity or cause protein degradation. Rather, high fold purification yielded high activity enzyme.

The ion exchange steps removed the remaining tannin and the bulk of contaminating protein while the affinity column steps highly enriched the preparation. The specific activities of the purified isozyme ranged from 56.4 to 106.2 units per milligram per minute (X= 78.7, S.D.=24.4, N=5), pH =5.0, and from 102.5 to 190.5 units per milligram per minute (X =145.7, S.D.=35.3, N=5), pH =6.0. The specific activities of these preparations far exceed those previously reported (2,5). There was a 370 fold purification with an average recovery of 25%. The enzyme was stable at 4° C. for several months with less than 10% loss of activity. The purified enzyme is stable in the presence or absence of Tween 80.

Figure 1B:
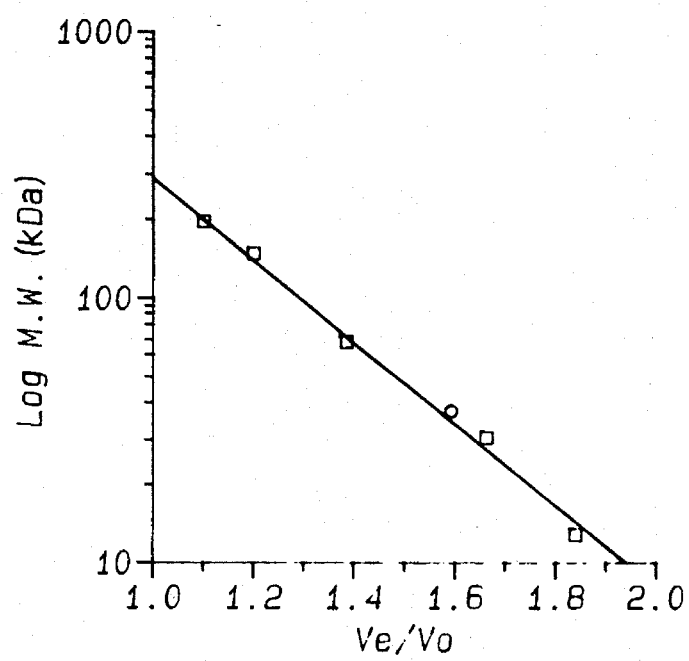

The mean molecular weight as determined by SDS PAGE under reducing and nonreducing conditions, was 36.7 kDa (S.D.=2.3, N=11) and 32.6 kDa (S.D.=1.7, N=8), respectively, FIG. 1a. The purified preparations had a single detectable band on a 12% Coomassie stained SDS gel. The native molecular weight was 34.0 kDa as determined by gel filtration on Sephacryl S-200, FIG. 1b. SDS PAGE and enzymatic activity measurements were performed on the S-200 column fractions, and the amount of enzymatic activity in the peak fractions correlated with the staining intensity of the 36.7 kDa band.

Amino acid composition data is presented in Table 2. The molecular weight calculated from compositional data was 37.4 kDa. The pI was approximated by chromatofocusing. The chromatographed preparation showed a single activity peak eluting with a mean pH of 7.03 (S.D.=0.16, N=4).

In activity tests on a variety of substrates, specificity was shown against PNP and 4-MU α-D-galactose conjugates. There was a mean Km of 0.26 mM (S.D.=0.09, N=3) for PNP-α-D-galactopyranoside. Sugars, other than α -D-galactose, showed no activity, as shown in Table 3. The absence of neuraminidase activity is important if the isozyme is to be used to modify blood group antigens. Removal of neuraminic acid residues from erythrocyte membranes results in rapid clearance by the reticuloendothelial system (16). α-L-fucosyl, β-D-galactosyl, α-N-acetyl-D-galactosaminyl, and β-N-acetyl-D-galactosaminyl residues are also abundant terminal saccharide residues on cell membranes. The isozyme preparations lacked the corresponding glycosidase activities.

Figure 2A:
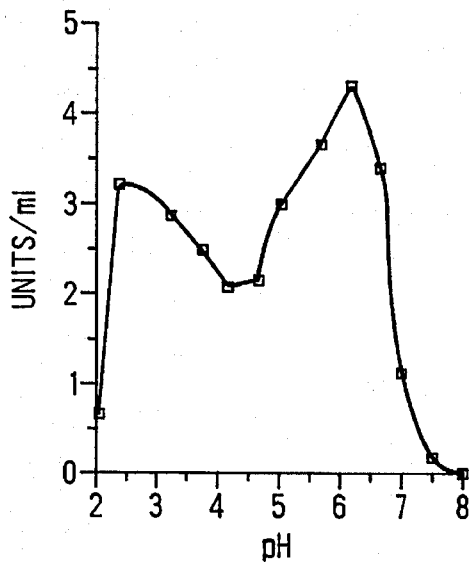
FIG. 2a is a graph showing isozyme activity as a function of pH.
Figure 2B:
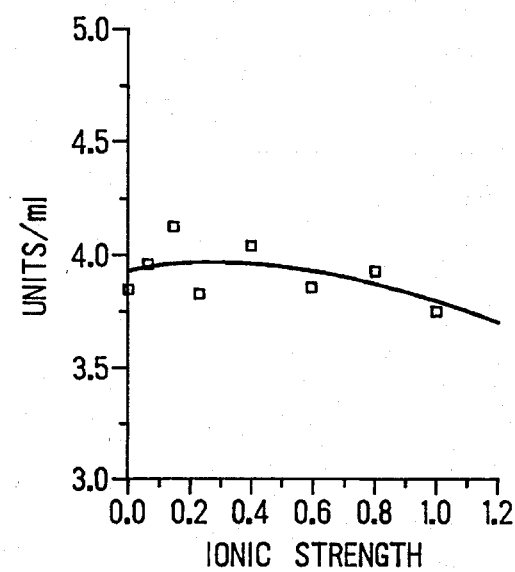
FIG. 2b is a graph showing isozyme activity as a function of ionic strength, with data points in FIGS. 2a and b showing the mean of six independent determinations.

The isozyme had a broad pH optimum at 6.3, FIG. 2a. The isozyme was not strongly inhibited by high or low ionic strengths at pH 6.0, FIG. 2b. Isozyme activity at pH = 6.0 and at an ionic strength of 0.15 are important properties which make this isozyme particularly useful for the enzymatic conversion of type B to type O erythrocytes.

No proteolytic activity was detected in the purified preparations. Aminopeptidase activity was below the limits of detection, ≦0.05 units/mg isozyme, with the following substrates: PNA-alanine, PNA-lysine, PNA-leucine, PNA-proline, and PNA-alanine-valine. In a resorufin-labeled casein assay with a sensitivity limit of 0.01 trypsin BAEE units, ≦0.01 BAEE units/mg isozyme was detected. This corresponded to less than 0.78 ng of endoprotease or "trypsin-like activity" per mg of pure isozyme. If exoglycosidase modified erythrocytes are to be used for transfusion, production of isozyme free of proteolytic activity is essential.

Figure 3A:
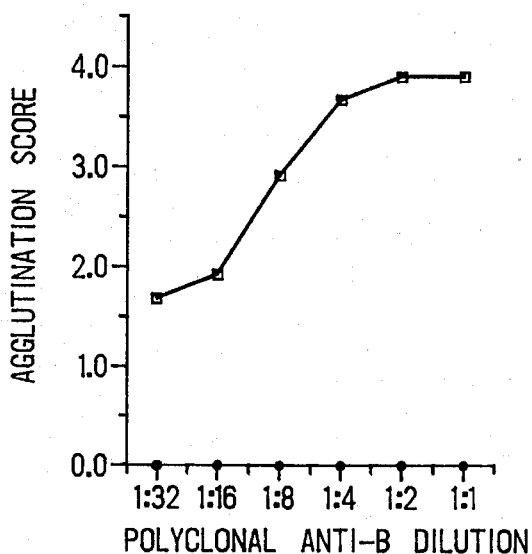
FIG. 3a is a graph showing isozyme activity against blood group B erythrocyte terminal α-D-galactosyl residues.
Figure 3B:
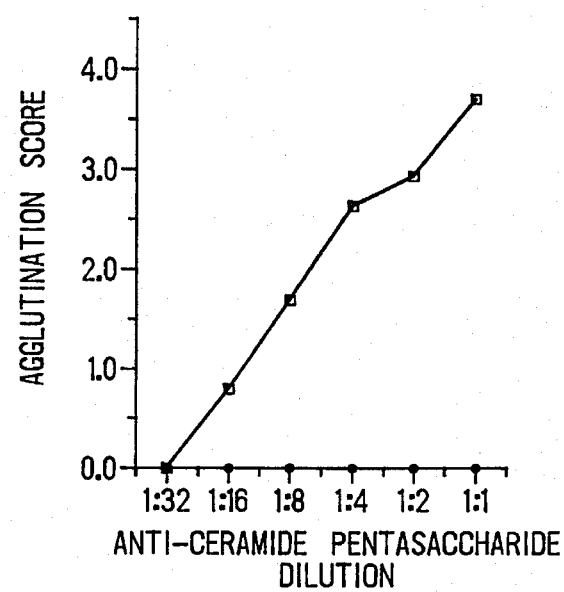
FIG. 3b is a graph showing isozyme activity against rabbit erythrocyte pentasaccharide ceramide terminal α-D-galactosyl residues (in FIGS. 3a and b, □=-α-D-galactosidase and ◊=+α-D-galactosidase) wherein 0=no agglutination and 4 indicates complete agglutination, all data points in FIGS. 3a and b being the mean of six independent determinations.

The enzyme was tested on high molecular weight substrates with terminal α-D-galactosyl residues. Removal of the terminal α-D-galactosyl epitopes from human erythrocyte blood type B antigen [gal(α1-3) gal(β1-R) [fuc(α1-2)] gluNAc(β1-R)] and rabbit erythrocyte pentasaccharide ceramide [gal(α1-3) gal(β1-4) gluNAc(β1-3) gal(β1-4) glu(α1-)ceramide] was achieved by the isozyme as shown in FIG. 3a and 3b (gal=galactose, glu=glucose, gluNAc=N-acetyl-glucosamine, and fuc=fucose).

The above data shows that the process of the present invention provides a highly purified isozyme of α-D-galactosidase having activity significantly greater than that reported in the prior art. This highly purified isozyme possesses significant utility in the field of red blood cell conversion.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES

1. Flowers, H., and Sharon, N. (1979) Advan. Enzymol. 48. 29–95.
2. Corchete, M., and Guerra, H. (1987) Phytochemistry 26. 927–932.
3. Yatziv, S. and Flowers, H. (1971) Biochem. Biophys. Res. Comm. 45. 514–518.
4. Courtois, J., and Petek, F. (1966) Methods Enzymol. 8. 565–570.
5. Lenny, L., Hurst, R., Goldstein, J., Benjamin, L., and Jones, R. (1991) Blood 77. 1383–1388.
6. Harpaz, N., Flowers, H., and Sharon, N. (1975) Arch. Biochem. and Biophys. 170. 676–683.
7. Goldstein, J., and Swain, T. (1965) Phytochemistry. 4. 185–192.
8. Harpaz, N., and Flowers, H. (1974) Methods Enzymol. 34. 347–350.
9. Bradford, M. (1976) Anal. Biochem. 72. 248–254.
10. Dean, K., and Sweeley, E. (1977) In Practical Enzymology of The Sphingolipidoses (Glew, R., and Peters, S., Eds.), 202–204, Alan R. Liss, Inc., New York.
11. Laemmli, U. (1970) Nature 227. 680–685.
12. Moore, S., and Stein, W. (1954) J. Biol. Chem. 211. 907–913.
13. Twining, S. (1984) Anal. Biochem. 143, 30–34.
14. Bryant, N. (1982) In Immunohematology. 280–297. W. B. Saunders, Philadelphia, Pa.
15. Hagerman, A. (1989) In Chemistry and Significance of Condensed Tannins (Eds. Hemingway, R., and Karchesy, J.). 323–334. Plenum Press, New York.
16. Gutowski, K. Linseman, D., and Aminoff, D. (1988) Carbohydr. Res. 178. 307–313.

TABLE 1

Summary of α-D-galactosidase isozyme purification.

| STEP | PROTEIN (mg) | TOTAL ACTIVITY (μMOLE/MIN) | YIELD (%) | SPECIFIC ACTIVITY (μMOLES/MG/MIN) | PURIFICATION (FOLD) |
| --- | --- | --- | --- | --- | --- |
| 1 | 3141.3 | 720.7 | 100.0 | 0.2 | 1.0 |
| 2 | 401.7 | 313.3 | 43.4 | 0.8 | 4.0 |
| 3 | 67.2 | 285.0 | 39.5 | 4.2 | 21.0 |
| 4 | 2.5 | 182.9 | 25.4 | 74.1 | 370.0 |

Data is expressed as the mean value from three different preparations.

TABLE 2

Amino acid composition of α-D-galactosidase isozyme.

| AMINO ACID | RESIDUES* MOLE | AMINO ACID | RESIDUES* MOLE |
| --- | --- | --- | --- |
| ASP | 47 | MET | 9 |
| THR | 22 | ILE | 16 |
| SER | 33 | LEU | 33 |
| GLU | 21 | TYR | 12 |
| PRO | 15 | PHE | 7 |
| GLY | 35 | LYS | 23 |
| ALA | 35 | HIS | 6 |
| CYS | 5 | ARG | 12 |
| VAL | 21 | | |

*Residues per mole expressed in integer values.

TABLE 3

Substrate specificity of α-D-galactosidase isozyme.

| SUBSTRATE | RELATIVE ACTIVITY* (%) |
| --- | --- |
| PNP-α-D-galactophyranoside | 100.00 |
| PNP-α-L-arabinopyranoside | <0.06 |
| PNP-N-acetyl-α-D-galactosaminide | <0.06 |
| PNP-N-acetyl-β-D-galactosaminide | <0.06 |
| PNP-N-acetyl-α-D-glucosaminide | <0.06 |
| PNP-N-acetyl-β-D-glucosaminide | <0.06 |
| PNP-α-L-fucopyranoside | <0.06 |
| PNP-β-L-fucopyranoside | <0.06 |
| PNP-β-D-galactopyranoside | <0.06 |
| PNP-α-D-glucopyranoside | <0.06 |
| PNP-β-D-glucopyranoside | <0.06 |
| 4-MU-α-D-galactopyranoside | 100.00 |

TABLE 3-continued

Substrate specificity of α-D-galactosidase isozyme.

| SUBSTRATE | RELATIVE ACTIVITY* (%) |
|---|---|
| 4-MU-N-acetyl-α-neuraminic acid | <0.01 |

*Relative activity is expressed as % of the activity of the isozyme on the corresponding α-D-galactopyranoside conjugate.

What is claimed is:

1. A process for purifying a *Coffea canephora* α-D-galactosidase isozyme by 1) homogenizing coffee beans containing the isozyme with an extraction buffer and obtaining a supernatant containing the isozyme and tannin, 2) extracting tannin from the supernatant by exposing the supernatant to insoluble polyvinylpolypyrrolidone (PVPP) in an amount sufficient to remove tannin from the supernatant by forming hydrogen bonds with the tannin, and 3) isolating the isozyme from the supernatant from which tannin has been removed.

2. A process as set forth in claim 1 wherein in said step 1) the extracting buffer contains the PVPP and the PVPP is present for extraction of tannin in step 2).

3. A process as set forth in claim 2 wherein said extraction buffer is a sodium citrate buffer containing said PVPP.

4. A process as set forth in claim 2 wherein said sodium citrate buffer is 0.1 to 500 mM.

5. A process as set forth in claim 4 wherein said sodium citrate buffer is 25 mM.

6. A process as set forth in claim 4 wherein sodium citrate buffer is 2.0 to 10.0 pH.

7. A process as set forth in claim 6 wherein said sodium citrate buffer is pH 5.0.

8. A process as set forth in claim 3 wherein said sodium citrate buffer contains 0.01 to 20% of said PVPP by weight.

9. A process as set forth in claim 8 wherein said sodium citrate buffer contains 10% of said PVPP.

10. A process as set forth in claim 1 wherein said step (2) of extracting tannin includes forming a precipitate containing the tannin and PVPP from the supernatant, step (3) is carried out by forming a precipitate of the isozyme by the addition of ammonium sulfate, resuspending the precipitate in buffer containing Tween 80, and dialyzing against the same buffer.

11. A process as set forth in claim 10 wherein the buffer containing the Tween 80 is a sodium citrate buffer.

12. A process as set forth in claim 11 wherein the sodium citrate buffer is 0.1 to 500.0 mM.

13. A process as set forth in claim 12 wherein the sodium citrate buffer is 20.0 mM.

14. A process as set forth in claim 11 wherein the buffer contains 0.0001 to 1 percent Tween 80 by weight/volume.

15. A process as set forth in claim 14 wherein the buffer contains 0.1 percent Tween 80.

16. A process as set forth in claim 11 wherein the buffer is pH 3.0 to 9.0.

17. A process as set forth in claim 16 wherein the buffer is pH 7.0.

18. A process as set forth in claim 1 wherein said process is carried out at a temperature range of 1.0 to 37.0° C.

19. A process as set forth in claim 18 wherein said temperature is maintained at 4° C.

* * * * *